(12) United States Patent
Hudak

(10) Patent No.: US 6,836,060 B2
(45) Date of Patent: Dec. 28, 2004

(54) AIR COOLED GAS DISCHARGE DETECTOR

(75) Inventor: George J. Hudak, Kennett Square, PA (US)

(73) Assignee: Agilent Technologies, Inc., Palo Alto, CA (US)

(*) Notice: Subject to any disclaimer, the term of this patent is extended or adjusted under 35 U.S.C. 154(b) by 84 days.

(21) Appl. No.: 09/817,669

(22) Filed: Mar. 26, 2001

(65) Prior Publication Data

US 2002/0135282 A1 Sep. 26, 2002

(51) Int. Cl.$^7$ .......................... H01J 17/26; H01J 61/28; B23K 9/00
(52) U.S. Cl. .............................. 313/231.31; 219/121.49
(58) Field of Search .................. 219/121.48, 121.49, 219/678; 313/231.31; 315/111.21, 111.18; 356/316; 73/28.02; 118/723

(56) References Cited

U.S. PATENT DOCUMENTS

| | | | | |
|---|---|---|---|---|
| 3,678,327 A | * | 7/1972 | Schmidt | .................... 315/5.39 |
| 4,482,246 A | * | 11/1984 | Meyer et al. | ................ 356/316 |
| 4,654,504 A | * | 3/1987 | Sullivan et al. | ......... 219/121.48 |
| 4,933,650 A | * | 6/1990 | Okamoto | ................. 333/99 PL |
| 5,051,557 A | * | 9/1991 | Satzger | .................. 219/121.52 |
| 5,086,255 A | * | 2/1992 | Okamoto et al. | ........ 315/111.21 |
| 5,216,330 A | * | 6/1993 | Ahonen | .................. 250/423 R |
| 5,625,259 A | * | 4/1997 | Holber et al. | ........ 118/723 MW |
| 6,057,645 A | * | 5/2000 | Srivastava et al. | ....... 315/111.21 |
| 6,263,830 B1 | * | 7/2001 | Kamarehi et al. | ........... 439/801 |

* cited by examiner

Primary Examiner—Joseph Williams
Assistant Examiner—Peter Macchiarolo

(57) ABSTRACT

A method for cooling the discharge tube in a gas discharge or atomic emission detector is described. An air cooled discharge detector is also disclosed. In the method and the detector, air is passed over the outer surface of the discharge tube thereby cooling the outer and inner surface of the discharge tube. Air cooling is utilized in any gas discharge detector including radio frequency powered atomic emission detectors.

4 Claims, 2 Drawing Sheets

6,836,060 B2

AIR COOLED GAS DISCHARGE DETECTOR

TECHNICAL FIELD

The invention relates to a new method and mechanism for cooling a gas discharge tube on an atomic emission detector. More specifically, the instant invention relates to a method and mechanism for cooling a discharge tube employed in an atomic emission detector that is cooled using air as the coolant.

BACKGROUND ART

One type of detector used in chromatographic systems is the atomic emission detector, alternatively referred to as a gas discharge detector. Atomic emission detectors employ the use of a gas discharge tube oriented to receive the effluents passing out of a chromatography column. The effluents entering the discharge tube are energized into excited atoms or molecules. As the electrons of the excited atoms or molecules return to their ground state, a characteristic light is emitted that is unique to an element or molecular bond. In a gas discharge detector, the light emitted as effluents enter the discharge tube is detected and can be plotted as a function of time.

A plasma generator, such as those powered by radio frequency (RF) or microwave energy, is utilized to provide energy to cause a plasma discharge to be formed in the discharge tube. In a typical application, energy is confined in a discharge tube whose dimensions are on the order of 1 mm diameter by 5 to 10 mm in length. This large amount of energy, in the form of heat, must be effectively removed or rapid degradation of the discharge tube results. Additionally, excess heat in the gas discharge tube can have a negative effect on the accuracy of the analysis.

Several techniques have been used to address this problem. However, each technique has disadvantages. In one technique, the power is reduced resulting in a reduction of excess heat. This method has been found to be unsatisfactory because the sensitivity of the detector is reduced.

Another technique uses water as a coolant. The design of this detector is described in U.S. Pat. No. 4,654,504 entitled "Water-Cooled Gas Discharge Detector". Several disadvantages are associated with the use of water as a coolant. First, water restricts the materials that may be used to construct components of the detector that come in contact with the water. Typically, stainless steel parts are used to avoid rusting or other degradation of the material caused by contact with water. Stainless steel is difficult and expensive to machine compared to other materials such as copper, brass, or aluminum. Second, the water itself is an operational expense if not recirculated. Water is discarded at a rate of approximately one liter per minute. Alternatively, the water can be recirculated but a recirculating system is also expensive. Recirculating system requires a water pump capable of one liter per minute flow, a water reservoir, and a heat exchanger.

A significant disadvantage to using water as coolant is the inevitable down time of the detector. Many components in atypical gas flow system, such as gauges, valves, restrictors, and filters, can be damaged by exposure to water. Damage to these components may cause equipment failure requiring that replacement parts be installed. Additionally, water may contaminate the gas system leads requiring that the leads be allowed to bleed out until hydrogen and oxygen emissions drop. The detector cannot be in operation while these remedial measure are performed.

Finally, the use of water in an electrical instrument is generally undesirable due to the inevitable occurrence of electrical shorts and other problems.

SUMMARY OF THE INVENTION

A method for cooling the discharge tube in a gas discharge detector is described. This method uses air as the coolant fluid. The use of air minimizes or eliminates many disadvantages of previous cooling methods. An air cooled discharge detector is also disclosed.

In the method of the present invention, air is passed over the outside surface of the discharge tube thereby cooling the outside surface of the discharge tube, which causes cooling of its inside surface. The air can be supplied from various sources. Typical sources include central compressors commonly found in laboratories or on board air pumps. The only requirement of the air supply is that it must be capable of delivering a sufficient volume of air to cool the discharge tube.

DISCLOSURE OF THE INVENTION

A method for air cooling the gas discharge tube of a gas discharge detector is disclosed. A flow of air is brought into contact with the outer surface of the gas discharge tube. The air flows at a velocity high enough to sufficiently cool the discharge tube. A gas discharge detector utilizing this method is also disclosed.

The advantages of using air as the cooling fluid are many and may include the following examples. Air cooling a gas discharge detector requires few components and can be done inexpensively. Air cooling increases the possible selection of materials from which detector components may be constructed. Air cooling cannot be the source of a spill and cannot contaminate the plasma gas system. Finally, air is a more desirable coolant in an electronic analytical instrument than water.

Figure 1:
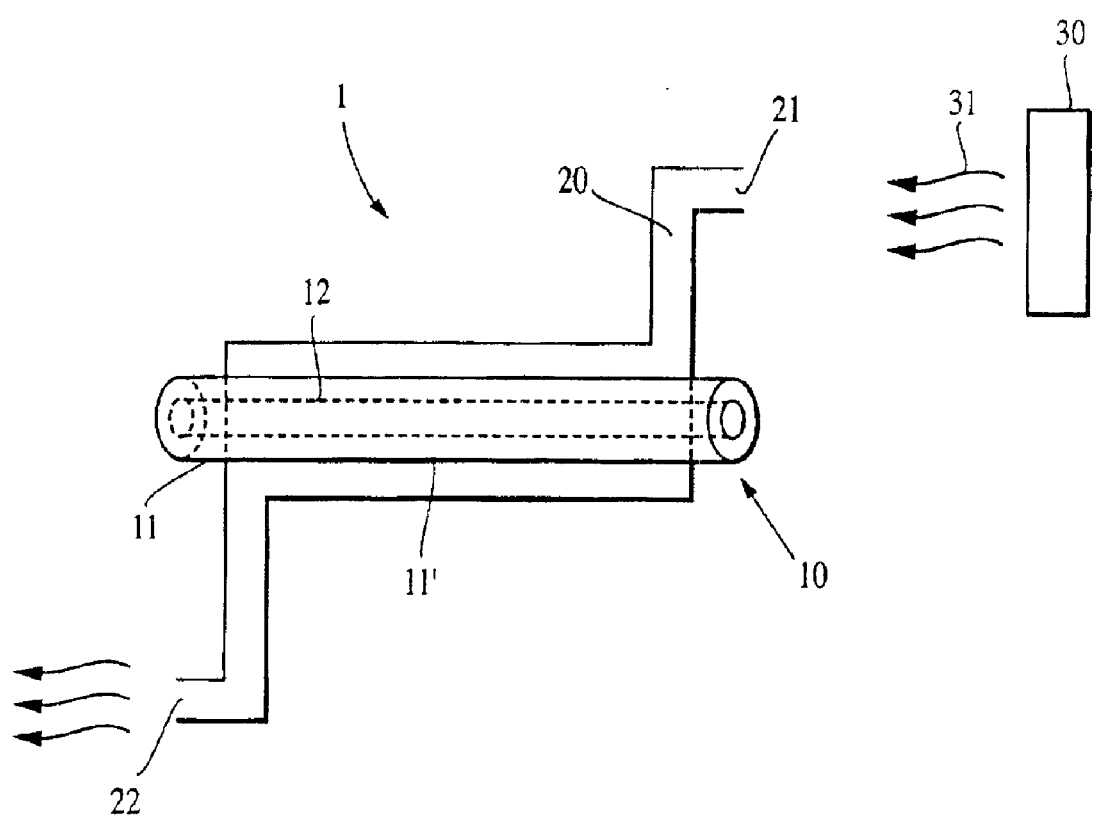
FIG. 1 illustrates a cooling mechanism of a gas discharge detector.

FIG. 1 illustrates an end-to-end view of a cooling mechanism 1 of a gas discharge tube 10. The cooling mechanism 1 contains an air passageway 20 and a source 30 for generating air flow 31.

The discharge tube 10 is made of a material with a high melting point and high chemical inertness. The discharge tube 10 has an outer surface 11 and an inner surface 12. The preferred material is sapphire, however other materials are acceptable such as boron nitride.

The air passageway 20 has an entry aperture 21 that is positioned to allow ingress of the air flow 31 from the source 30. The air passageway 20 also has an exit aperture 22 that allows egress of the air flow 31. The air passageway 20 extends from the entry aperture 21 to the exit aperture 22. The air passageway 20 is positioned such that a portion of the air passageway 20 is exposed to at least a portion 11' of the outer surface 11 of the discharge tube 10. The air passageway 20 as shown has a cylindrical shape, however the air passageway 20 can have any cross-sectional shape and any configuration that provides a flow of air over at least a portion 11' of the outer surface 11 of the discharge tube.

In operation, the source 30 generates air flow 31. The air flow 31 functions as a coolant. The air flow 31 enters the entry aperture 21 and travels through the passageway 20.

While in residence in the passageway 20, the air flow 31 is in contact with the outer surface 11 of the gas discharge tube 10. The air flow 31 cools the outer surface 11 of the discharge tube 10 which in turn cools the inner surface 12 of the discharge tube 10. The air flow 31 then exits through aperture 22.

The radial thickness of the passageway 20 will vary according to instrument design. The radial thickness must be large enough to allow a sufficient air flow 31 velocity to effectively cool the outer surface 11 of the discharge tube 10, and in turn, cause sufficient cooling of the inner surface 12 of the discharge tube 10. Similarly, the amount of exposure between the outer surface of the discharge tube 10 and the passageway 20 will vary according to instrument design. There must be sufficient exposure between the outer surface 11 and the passageway 20 to effect cooling of the discharge tube 10.

An air-cooled discharge detector also contains other components necessary for operation of a gas discharge detector. These other components are the standard components necessary for the operation of a gas discharge detector and are commonly known in the art.

Figure 2:
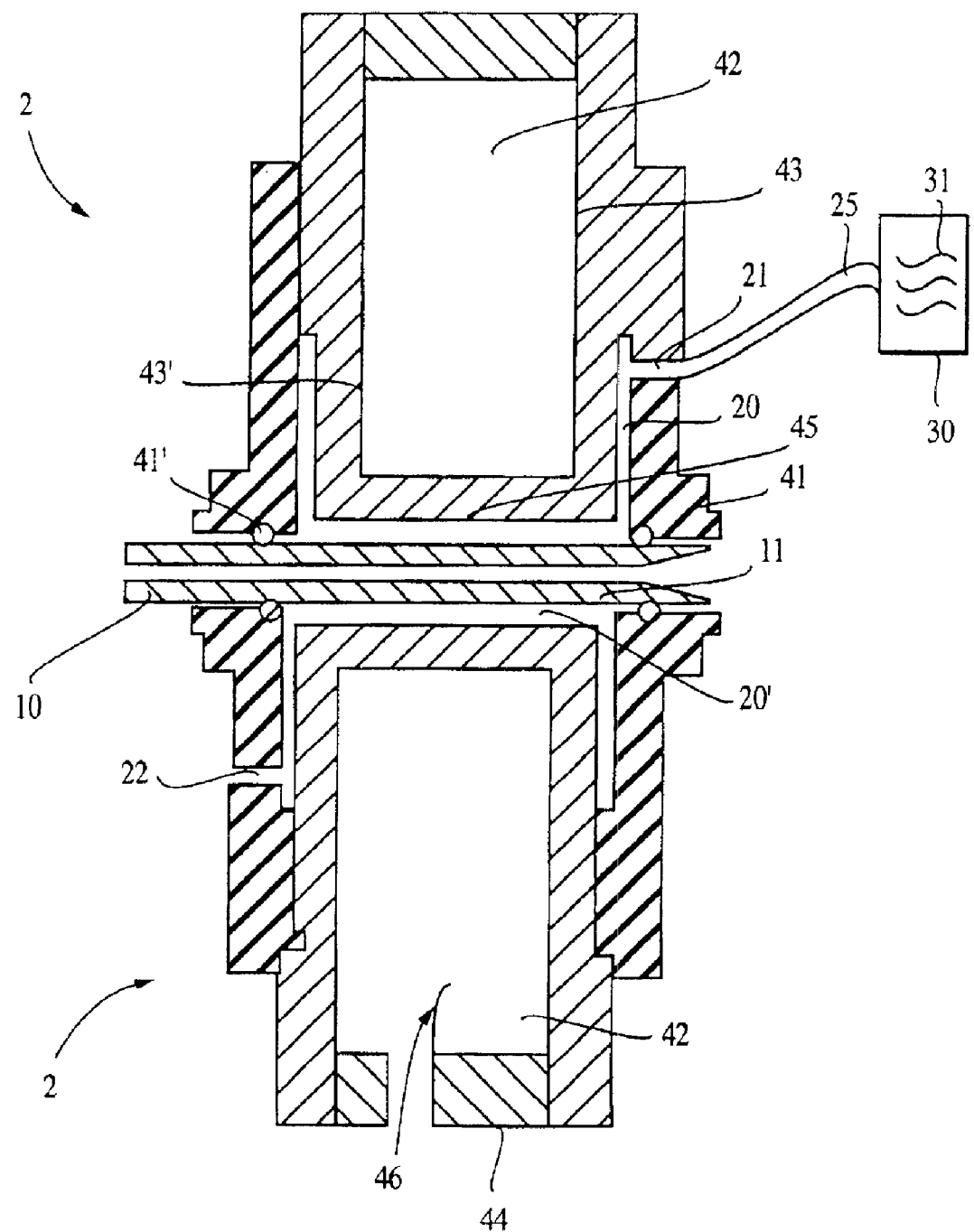
FIG. 2 depicts an air-cooled gas discharge detector.

FIG. 2 illustrates an embodiment of an air cooled gas discharge detector 2. In FIG. 2, an air-cooled gas discharge detector 2 uses radio frequency or microwave powered plasma. The radio frequency or microwave energy is generated by a magnetron or other acceptable source. Energy is introduced into a cavity 42 that surrounds the circumference of the gas discharge tube 10. A technique for constructing the cavity 42 and mounting a gas discharge tube within the cavity 42 are described in U.S. Pat. No. 4,654,504 entitled "Water-Cooled Gas Discharge Detector" and is incorporated herein by reference as if fully set forth. The cavity is defined by side walls 43 and 43', an outerwall 44, and an inner wall 45. Microwaves are introduced into the cavity 42 via a probe 46 through the outer wall 44. The inner wall 45 surrounds the outer surface 11 of the gas discharge tube 10. The radius of the innerwall 45 is larger than the outer radius of the gas discharge tube 10. The innerwall 45 of the cavity 42 is mounted to form a separation between the outer surface 11 of the gas discharge tube 10 and the innerwall 45 of the cavity 42. The separation forms the portion 20' of the passageway 20 that is exposed to the outer surface 11 of the gas discharge tube 10. The gas discharge tube 10 is sealed inside the detector 1 using, for example, O-rings 41 and 41'. O-rings 41 and 41' are preferably made of silicon rubber but can be made of other materials such as graphite.

In the exemplary embodiment, the entry aperture 21 and the exit aperture 22 are on opposite sides of the detector 1, however other placements are possible. The cross-sectional dimension of the entry aperture and exit aperture is preferably three to seven millimeters. The cross-sectional dimension of the entry aperture 21 and exit aperture 22 can be smaller than three millimeters but should not be narrower than the radial thickness of the passageway 20. This ensures that the entry aperture 21 and exit aperture 22 do not significantly contribute to head pressure when air flow 31 is introduced. The cross-sectional dimension of the entry aperture 21 and exit aperture 22 may be larger than seven millimeters and is limited only by detector design constraints. The radial thickness of the portion 20' of the passageway 20 that surrounds the outer surface 11 of the gas discharge tube 10 is preferably the narrowest portion of the passageway 20. The portion 20' of the passageway 20 that surrounds the outer surface 11 of the gas discharge tube 10 is preferably ten to forty thousandths of an inch but can be thinner or thicker so long as the air flow 31 can be maintained at a sufficient velocity to cool the discharge tube 10. In the embodiment shown, the passageway 20 also extends along the outer surface of the side walls 43 and 43' that form the cavity 42.

In operation, the air flow 31 in the preferred embodiment is approximately 10 liters per minute. At this rate, sufficient cooling of a sapphire discharge tube 10 is achieved. Lower air flow 31 rates may be used so long as the discharge tube is sufficiently cooled. The amount of air required to cool the discharge tube will vary depending on the detector. Factors that affect the required air flow include, for example, the operating temperature and material of the discharge tube. In an application in which air is replacing water as the coolant fluid, the volume of air required per minute is about ten times the amount of water required. The increased volume of air will compensate for the difference in heat capacities between air and water. In a typical detector, the air flow needs to be about 5 to 10 liters per minute, for example. Other air flow rates can be used depending upon, for example, the configuration and requirements of a particular detector.

In the preferred embodiment, the source 30 of the air flow 31 is connected to the entry aperture 21 by tubing 25. The tubing 25 is connected to the entry aperture 21 preferably using a barbed fitting and a hose clamp but other types of conventional connectors are possible such as a swage lock, screw fitting or national pipe thread, or friction fit. The tubing 25 is also connected to the air supply 30 by conventional methods such as a barbed fitting and a hose clamp, swage lock, screw fitting, or friction fit. Other systems or mechanisms may be used for introducing air flow 31 into the entry aperture 21 so long as the air flow 31 through passageway 20 is maintained at a sufficient velocity to provide the required or desired cooling. The source 30 is house gas or laboratory gas from a central compressor but can be any source of air that provides a sufficient supply of air including an on board air pump. For purposes herein, "Air" is defined as any gas or combination of gasses. Atmospheric air is the preferred coolant, because it is safe and readily available, however, other gasses, such as nitrogen or argon, or other combination of gasses could be used.

Air cooling of the discharge tube in a gas discharge detector can result in comparable discharge tube life to that of a water cooled discharge detector and may provide other advantages as identified above.

What is claimed is:

1. A gas detector comprising:

a discharge tube made of sapphire in which gas is carried for conversion to a plasma therein; and a radial resonator having a chamber therein and having a central passageway extending axially there thorough which cooling air moves, the discharge tube extending through the central passageway so that the cooling air comes in contact with the external surface of the discharge tube, the radial resonator when energized subjecting the discharge tube with sufficient amounts of radio frequency or microwave energy to generate plasma from the gas in the discharge tube, such radio frequency or microwave energy not effecting the cooling air.

2. The gas detector of claim 1 wherein the radial resonator subjects the discharge tube and enclosed passageway with sufficient amounts of microwave energy to generate plasma in the discharge tube from the gas, such microwave energy not effecting the cooling air.

3. The gas discharge detector of claim 1 wherein the gas discharge tube is no more than 10 millimeters in length.

4. The gas discharge detector of claim 3 wherein the gas discharge tube has a diameter on the order of 1 mm.

* * * * *